United States Patent
Silwanowicz et al.

[11] Patent Number: 6,077,254
[45] Date of Patent: *Jun. 20, 2000

[54] ABSORBENT GARMENT WITH CONTAINMENT POCKET

[75] Inventors: Anthony Silwanowicz; Penny C. Lovestedt, both of Renton; John R. Cook, Tacoma, all of Wash.

[73] Assignee: Paragon Trade Brands, Inc., Norcross, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,201

[22] Filed: Aug. 23, 1996

Related U.S. Application Data

[63] Continuation of application No. 08/273,958, Jul. 12, 1994, abandoned.

[51] Int. Cl.[7] .................................................. A61F 13/15
[52] U.S. Cl. .................................. 604/385.2; 604/358
[58] Field of Search ................................ 604/358, 385.1, 604/385.2

[56] References Cited

U.S. PATENT DOCUMENTS

| | | |
|---|---|---|
| 4,507,163 | 3/1985 | Menard . |
| 4,662,877 | 5/1987 | Williams . |
| 4,726,807 | 2/1988 | Young et al. . |
| 4,738,677 | 4/1988 | Foreman . |
| 4,764,234 | 8/1988 | Smits et al. . |
| 4,795,451 | 1/1989 | Buckley . |
| 4,801,345 | 1/1989 | Dussaud et al. . |
| 4,834,737 | 5/1989 | Khan . |
| 4,915,767 | 4/1990 | Rajala et al. . |
| 4,917,746 | 4/1990 | Kons et al. . |
| 4,968,312 | 11/1990 | Khan . |
| 5,030,303 | 7/1991 | Cucuzza . |
| 5,092,861 | 3/1992 | Nomura et al. . |
| 5,147,487 | 9/1992 | Nomura et al. . |
| 5,197,960 | 3/1993 | Nomura et al. . |
| 5,213,645 | 5/1993 | Nomura et al. . |

FOREIGN PATENT DOCUMENTS

| | | | |
|---|---|---|---|
| 0563971A1 | 10/1993 | European Pat. Off. | ............ 604/385.2 |
| 2266444A | 4/1993 | United Kingdom . | |
| 2266444 | 11/1993 | United Kingdom | ................ 604/385.2 |

Primary Examiner—John G. Weiss
Assistant Examiner—Dennis Ruhl
Attorney, Agent, or Firm—Hunton & Williams

[57] ABSTRACT

A disposable absorbent garment having a backing layer, an inner layer, and an absorbent pad therebetween. The inner layer comprises an integral sheet having an opening extending therethrough through which exudates may move into a pocket formed between the backing and inner layers. A pair of elongate elastic members are secured to the inner layer in opposed, substantially mirror image curvilinear paths which overlap to encircle the opening. A method for producing such a garment also is described.

20 Claims, 2 Drawing Sheets

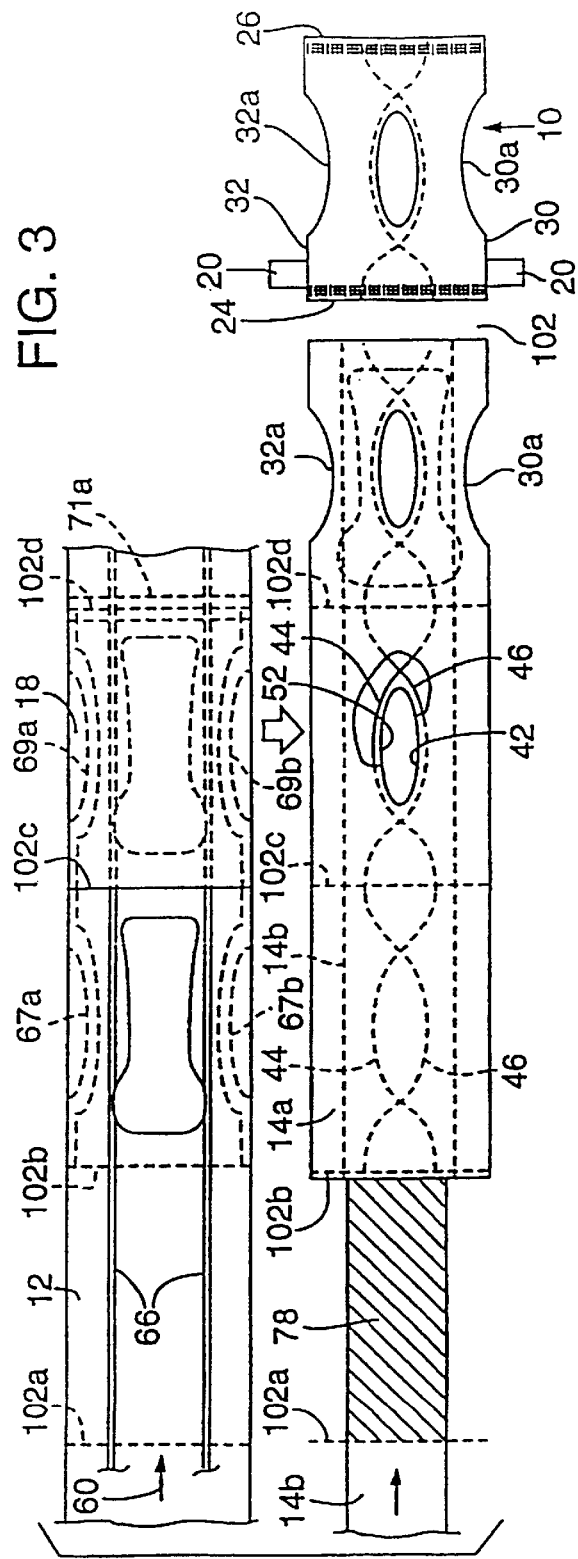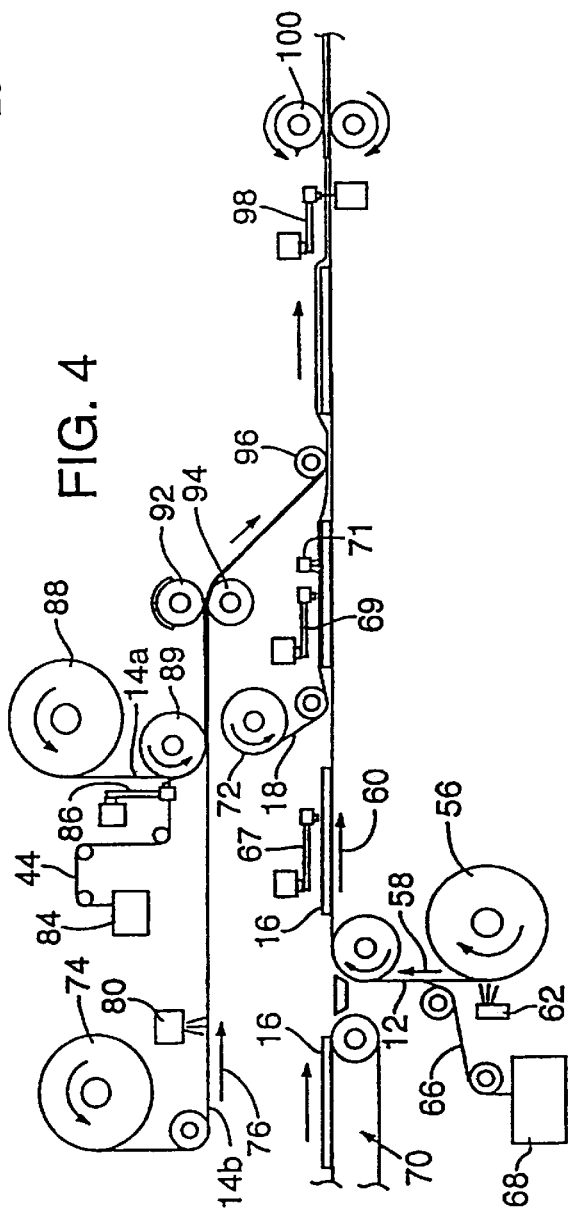

ABSORBENT GARMENT WITH CONTAINMENT POCKET

This application is a continuation, of application Ser. No. 08/273,958, filed on Jul. 12, 1994 now abandoned.

BACKGROUND OF THE INVENTION

The present invention relates generally to a disposable absorbent garment, such as a diaper or training pant, and more specifically to an improved garment design and method for producing the same, which provides a waste containment region.

The manufacture of disposable absorbent garments, such as infant diapers or training pants, and adult incontinence briefs, is well-known in the art. Traditionally, disposable diapers and other such products are constructed with a moisture-impervious outer or backing layer, a body-contacting inner layer, and a moisture-absorbent core layer sandwiched and encased between the inner and outer layers. More recently, elasticized waistbands, elasticized leg openings, and elasticized waist openings have been developed to provide a better fit and enhance the containment of bodily exudates.

A drawback of conventional prior absorbent garments is urine leakage from sides of the garment, and poor isolation or containment of fecal material. In some instances, prior absorbent garments have provided openings through the inner body-contacting layer of the garment through which exudates may pass in the crotch region of the garment, but for various reasons these have been constructed in such a manner that they either provide improper and inefficient contact with the wearer's body, or present other regions through which exudates may leak from the garment. Such prior article designs often have had poor fecal material containment or acceptance, such that fecal material may spread over the article and not be sufficiently isolated from the wearer.

Therefore, a need exists for an improved disposable absorbent garment design, suitable for use by wearers, which can be manufactured efficiently and which is not susceptible to the above and other limitations and disadvantages.

Some of the objections to and disadvantages of the prior art as known is that some provide openings in a liner sheet, but provide elastics located only along opposing sides of the opening. Consequently, areas of the liner sheet at the ends of the openings tend to remain somewhat flat against underlying structure and do not lift up to readily capture exudates migrating toward the ends of the product. Others in the prior art have attempted to produce products in which an inner liner sheet is composed of a pair of opposed side sheet strips having wide and narrow sections, with the strips then being secured to the top of the garment with their narrow sections facing to provide an opening. These may be difficult to produce and align in a high-speed manufacturing operation, and if not properly secured together in regions outside the opening can provide additional leakage passages for exudates.

SUMMARY OF THE INVENTION

It is an overall object of the present invention to provide an improved disposable absorbent garment design.

It is a further object of the present invention to provide a novel disposable absorbent garment which is economical to manufacture.

An additional object of the present invention is to provide a disposable absorbent garment which provides a containment pocket into which exudates may be passed through an opening and which thereby minimizes the escape of moisture and solids to the outer garments of a wearer.

It is a further object of the present invention to provide an absorbent garment design which provides effective containment of exudates while overcoming manufacturing complexities and inefficiencies found in the production of prior art garments.

It also is an object to provide a disposable absorbent garment designed to be constructed inexpensively and efficiently in a high-speed manufacturing system, while at the same time providing exceptional performance in containing and absorbing exudates.

According to one aspect of the present invention, a disposable absorbent garment is provided including a moisture-impervious outer layer or backing sheet, an inner layer or top sheet, and an absorbent layer sandwiched between the inner and outer layers. The garment has opposed front and back waist end edges and opposed side margins. The inner layer has a waste receiving opening extending therethrough between the first and second waist edges and the first and second side edges. First and second elongate elastic members are secured to the inner layer. The elastic members have first end portions spaced to opposite sides of the longitudinal axis of the garment adjacent the first waist edge and second end portion spaced to opposite sides of the longitudinal axis from each other adjacent the second waist edge. The elastic members extend in substantially mirror image intersecting curvilinear paths from the first end portions to the second end portions and along opposite side margins of the opening.

The elastic preferably bounds the entire perimeter of the opening, thus tending to lift the portions of the inner layer bounding the opening into contact with the wearer's body and providing a waste containment pocket within the garment. When the wearer voids, exudate is directed to the pocket formed between the inner layer and the absorbent pad where the exudate can be absorbed and contained. This minimizes leakage of the exudates at both the waist end edges and side edges of the garment.

In addition, the inner layer or top sheet, may be manufactured in an efficient manner by securing the first and second elastic members to the inner layer material in curvilinear paths in which the first and second elastic members are disposed in substantially sinusoidal curved paths and the opening is formed within a region bounded by overlapping portions of the sinusoidal curves of the elastics.

These and other objects, features and advantages of the present invention will become apparent to those skilled in the art from the following description and drawings.

BRIEF DESCRIPTION OF THE DRAWINGS

FIG. 3 is a schematic plan view of a method for manufacturing a garment as illustrated in FIG. 1, and according to the present invention.

FIG. 4 is a schematic side elevation view of apparatus which may be used in performing manufacturing methods for producing such a garment.

DETAILED DESCRIPTION OF PREFERRED EMBODIMENT

Figure 1:
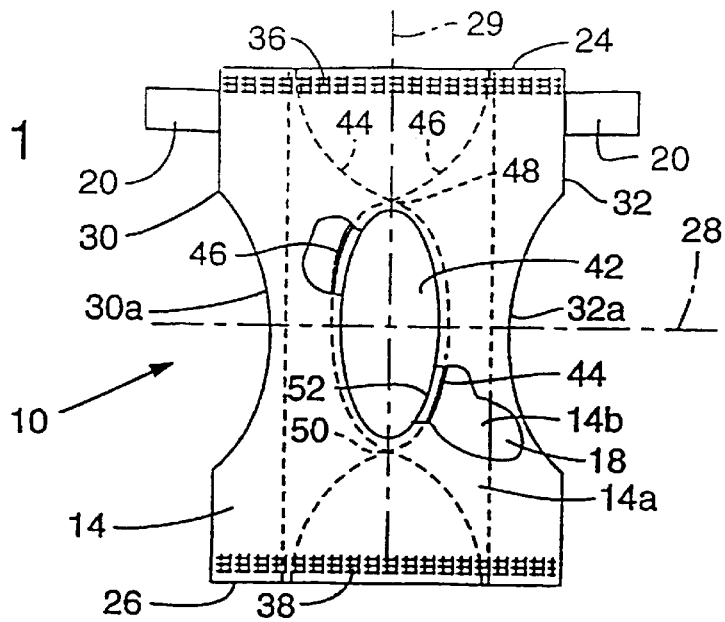
FIG. 1 is a developed plan view of an absorbent garment constructed according to an embodiment of the present invention.
Figure 2:
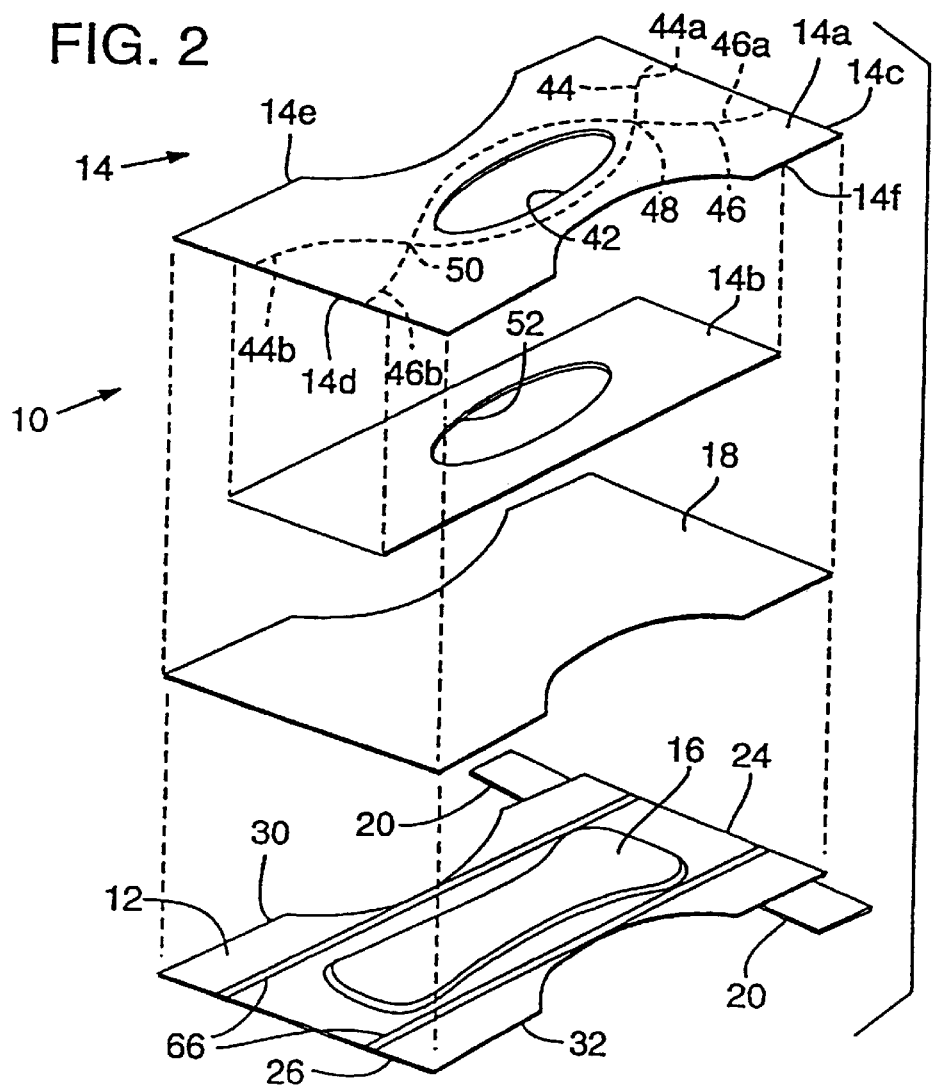
FIG. 2 is a perspective exploded view of the component parts of the garment illustrated in FIG. 1.

FIGS. 1 and 2 illustrate an embodiment of a disposable absorbent garment 10 manufactured in accordance with the invention having a moisture impervious outer, or backing, layer, or sheet, 12 and an inner, or liner, layer 14. A moisture-absorbent layer, core, or pad 16, is supported on backing layer 12. A moisture-pervious separator sheet 18 is disposed between inner layer 14 and pad 16. The layers, sheets and pad are sandwiched together in the disposition illustrated in FIG. 2, with pad 16 positioned between separator sheet 18 and backing layer 12 and inner layer 14 overlying separator sheet 18. The parts of the garment may be joined by adhesively or otherwise bonding the layers together in a conventional manner.

The core 16 typically is of wood pulp or other absorbent fibers with or without superabsorbent particles. The core also may be of a multi-layer construction. Such garments also typically may include outer leg gathers or seals, stretchable waistbands, and tapes or other fasteners at the waist. A pair of tape fasteners are indicated generally at 20 extending outwardly to opposite sides of the garment adjacent one of its ends.

The disposable absorbent garment 10 typically is used as a baby or infant diaper or as an adult incontinence brief. It also may be sealed or joined along opposed side edges to form a pull-on style training pant. The manufacture of such garments generally is known in the art. One garment and method of manufacture is illustrated in U.S. Pat. No. 4,726,807, which is incorporated by reference herein. Another example is set forth in U.S. Pat. No. 4,687,477 which also is incorporated herein by reference.

Due to the wide variety of core, top sheet and backing sheet constructions and materials, the invention is not intended to be limited to any specific materials or constructions of these components.

As exemplary material for the backing sheet, the moisture-impervious outer layer 12 may be of a thin thermoplastic material, such as a pigmented polyethylene film having a thickness in the range of 0.02–0.04 mm. The moisture-permeable separator sheet 18 may, as an example, be of a carded polyester fiber with a latex binder, or of a spun-bonded polypropylene having continuous fibers and thermally bonded by patterned calendar rolls, or a tissue. The moisture-absorbent core 16, in a preferred example, may be of wood fibers or other fibers such as chemical wood pulp, or any other suitable liquid-absorbing material, such as commercially available fluff pulp, or of a fluff bleached kraft soft wood pulp.

The inner, or liner, layer 14 is made up of two sheet layers, the major one of which is an integral main sheet 14a and the other being a cover sheet 14b. The main sheet layer 14a may be formed of a moisture-impervious material, preferably hydrophobic non-woven. Cover sheet 14b also may be a non-woven hydrophobic material similar to sheet 14a. In other embodiments the component sheets 14a, 14b may be gradient hydrophobic or hydrophilic, with one being more hydrophobic than the other to produce desirable surface dryness characteristics.

The garment 10 has a first laterally extending waist edge 24, and a second waist edge 26 spaced longitudinally therefrom. The waist edges are spaced to opposite sides of the transverse axis 28 of the garment. These waist edges may lie along front and back waist regions of the wearer during use. The garment also has opposed first and second side edges, or margins, 30, 32, respectively, spaced to opposite sides of longitudinal axis 29 of the garment. The side edges have incut leg regions 30a, 32a, which fit about the legs of a wearer during use. The garment thus has a generally hourglass-shaped configuration with tape fasteners 20 extending outwardly from opposite side margins, or edges, adjacent first waist edge 24.

Waist gathers 36, 38 are provided adjacent opposite waist edges 24, 26, respectively, by the application of elastic material extending transversely of the garment to provide a more comfortable fit for the wearer.

The core, or pad, 16 may assume a somewhat hourglass shape as illustrated, or simply may be rectangular or some other configuration. The edges of inner layer 14 may be coextensive with backing sheet layer 12 or may terminate at some point inwardly from the edges of the backing sheet, as desired.

Thus, the garment as illustrated in FIG. 1 typically has an overall hourglass shape. The top and bottom, or opposed waist edges 24, 26, form the respective front and back waist end portions of the garment. The crotch portion of the garment is central to the hourglass shape and has a narrower width than the waist edge portions.

This invention provides a new and improved disposable absorbent garment design for providing an opening to a compartment within the garment which provides an inner waste receiving area where exudates may be collected.

Referring to FIG. 2, and specifically to inner layer sheet 14a, it is an integral sheet which preferably would be composed of a non-woven hydrophobic material so as to be both soft and capable of directing exudates toward the liquid-pervious separator sheet 18 and into the containment pocket formed between inner layer 14 and backing layer 12. A material which may be used for producing sheet 14a is a spun-bond polypropylene material basis weight 20.3 grams per square meter, sold by Poly-Bond Corporation.

Sheet 14a has first and second waist edge regions 14c, 14d, and opposed side edges 14e, 14f consistent with those described for the garment in FIG. 1.

A substantially centrally located elongate oval opening 42 extends through sheet 14a with its long dimension extending longitudinally of sheet 14a. The opening is disposed substantially centrally in the crotch region of the sheet. Although the opening is illustrated as being oval, it should be recognized that other forms of openings may be used also.

Secured to one face of sheet 14a, and in this case the face directed toward outer layer 12, are first and second elongate elastic members 44, 46 (shown in dashed line). Each of the elastic members has a first end portion 44a, 46a, respectively, and second end portion 44b, 46b, respectively. The first set of end portions are disposed between the first waist edge 24 and the transverse axis of the garment and are spaced apart laterally to opposite sides of the longitudinal axis, or center line, of the garment. Similarly, the second end portions of the elastic members are disposed between the second waist edge 26 and the transverse axis of the garment and are laterally spaced apart to opposite sides of the longitudinal axis of the garment. The elastic members are secured to inner layer sheet 14a in substantially mirror-image overlapping sinusoidal curves which intersect, or cross over, each other at points 48, 50 adjacent opposite ends of opening 42. Portions of the elastic members 44, 46 between intersection, or crossover, points 48, 50 extend along opposite sides of opening 42 as illustrated in FIG. 2.

Describing in greater detail the paths taken by the elastic members as shown in FIGS. 1 and 2, member 44 has its first end portion 44a disposed adjacent the first waist edge region 24 of the garment and between the longitudinal axis and the first side edge 30 of the garment. Elastic member 44 extends from its first end portion across the longitudinal axis in a region between the first waist edge and opening 42. It then extends along the side of the opening adjacent the second side edge 32 of the garment, back across the axis between the opening and the second waist edge 26, and then terminates at second end portion 44b adjacent the second waist edge 26 and between the longitudinal axis and the first side edge 30 of the garment.

The second elongate elastic member 46 has its first end portion 46*a* disposed adjacent the first waist edge 24 and between the longitudinal axis of the garment and the second side edge 32. It extends from its first end portion across the longitudinal axis and across the first elastic at point 48 between the first waist edge and the opening. It then extends along a side of opening 42 adjacent the first side edge 30 and then returns to cross the first elastic member at point 50 between the opening 42 and the second waist edge. The second elastic then terminates at its second end portion 46*b* adjacent the second waist edge 26 and between the longitudinal axis and the second side edge 32 of the garment. The elastic members are disposed adjacent and at a substantially constant selected distance from the inner edge of the opening to provide the desired effect for controlling the position of liner layer 14.

The cover sheet 14*b* as shown in FIGS. 1 and 2 has a length corresponding to the length of the garment, but is somewhat narrower than sheet 14*a*. Since its purpose is to cover selected portions of the elastic members, its width is at least as great as the maximum elastic pattern width, and its length is sufficient to extend across both intersection points 48, 50. In some embodiments sheet 14*b* may be omitted.

Sheet 14*b* has an oval opening 52 formed therein. Opening 52 is substantially similar to opening 42 and is coincident with opening 42 when the sheets are secured together. Openings 42, 52 provide a through passage, or opening, into a containment pocket, or region, formed between inner layer 14 and backing sheet 12. The cover sheet 14*b* is secured, as by adhesive or other bonding methods, to the face of sheet 14*a* bearing the elastic members and covers the elastic members.

The elastic members are bonded to inner layer 14*a* in a stretched or tensioned condition. As used herein, the term "bonded" refers to adhesive bonding, sonic bonding, heat bonding, solvent bonding, stitching or any other method of affixation known or hereafter discovered. These elastic members urge the inner liner into contact with the wearer's body.

The elastic members may comprise materials such as natural rubber strands (either single or multiple strands), lycra strands, or others used in the industry.

A method and apparatus for producing a garment according to the invention is shown schematically in FIGS. 3 and 4. Initially, an elongate web of backing layer sheet material 12 is drawn from a roll 56 and carried longitudinally in the direction of arrows 58, 60. A spray device 62 places strips of adhesive on selected portions of sheet web 12 to which elastic members are to be applied.

Elongate elastic members 66 are drawn from a reservoir 68 and applied in stretched tensioned condition to the adhesive coated regions of sheet 12 as illustrated in FIG. 3 to form leg gathers for the garment. Pre-formed absorbent pads 16 are carried in longitudinally spaced relationship by a conveyor 70 to be placed atop sheet 12 and carried therewith in the direction of arrow 60.

A pair of swing arms style adhesive applicators adjacent opposite sides of the flow path for web 12, such as that indicated generally at 67 in FIG. 4, are positioned to oscillate horizontally over the path of backing sheet 12 to apply paths of adhesive. The adhesive paths or regions are indicated in dashed outline adjacent opposite sides of sheet 12 at 67*a*, 67*b* in FIG. 3.

Separator sheet material 18 is drawn in an elongate web from roll 72 and placed atop web 12 and pads 16. Sheet 18 is adhered to sheet 12 by the adhesive regions 67*a*, 67*b*.

A pair of horizontally swingable adhesive applying arms, such as that indicated at 69 in FIG. 4, are operable to apply paths of adhesive, such as that indicated at 69*a*, 69*b* in FIG. 3, atop separator sheet 18. A transversely extending adhesive sprayer 71 is operable to apply a transversely extending region of adhesive indicated generally 71*a* in FIG. 3. Such transversely extending region of adhesive is deposited on the material in each of the spaces between pads 16.

Concurrently with the assembly of the backing sheet web 12, absorbent pad 16, and separator sheet 18, the inner layer 14 is being produced. Initially, an elongate web of cover sheet material 14*b* is drawn from a roll 74 and carried longitudinally in the direction of arrow 76. The top surface of the cover sheet 14*b* has a pattern of adhesive 78 applied thereto (see FIG. 3) by an applicator 80. Although the adhesive pattern shown in FIG. 3 is substantially continuous along sheet web 14*b* with a width as great as the width of the sheet, it should be recognized that the adhesive may be applied in strips, swirls or otherwise, which may not need to be continuous along sheet 14*b*.

An elongate web of cover sheet material 14*a* is drawn from a roll 88, carried under a roller 89, and is applied atop cover sheet web 14*b*. Sheets 14*a*, 14*b* are joined together by the adhesive pattern 78 previously applied thereto.

Before sheet 14*a* is placed on sheet 14*b*, elastic members 44, 46 are applied to sheet 14*a*. Elastic members 44, 46 are drawn from a reservoir indicated generally at 84 and are applied to sheet 14*a* through spaced elastic applicators, such as vertically swingable, or oscillating, arm 86, in a tensioned, stretched pair of overlapping sinusoidal curves as previously described and as illustrated in FIG. 3. In the illustrated embodiment the curved elastics extend substantially continuously along the web and are adhered thereto by the pattern of adhesive deposited by an adhesive-applying head on arms 86.

The combined liner sheet 14, comprising webs 14*a*, 14*b* and elastic members 44, 46, passes through die-cutting rolls 92, 94 which cut openings 42, 52 through sheets 14*a*, 14*b*.

After formation of openings 42, 52 sheets 14*a*, 14*b* are pressed by roller 96 against the top of separator sheet 18 and are adhered, or joined, to the underlying combination at the regions of adhesive 69*a*, 69*b*, 71*a*. The inner layer 14 thus is joined in a substantially leak-free manner to backing sheet 12 and separator sheet 18 about the periphery of each garment to be produced.

Swing arm-style water jet cutters, such as that indicated generally at 98 in FIG. 4, cut out leg openings 30*a*, 32*a* which are outside the regions of joinder for the sheets in the composite product. A rotating knife 100 extending transversely of the apparatus cuts the combined product as indicated generally at 102 to separate a finished garment 10 from the products upstream therefrom, which are still in process. The cut is made substantially in the middle of the transverse regions joined by adhesive layer 71*a* so that the ends of the garments are sealed.

In FIG. 3, a plurality of transversely extending dashed lines 102*a*, 102*b*, 102*c*, 102*d* indicate lines along which component parts of the garment will be separated by rotating knife 100 to produce separate garments, such as that indicated generally at 10.

As is seen, the composite product produced will have the backing and inner layer sheets joined along opposite end edge regions 24, 26 and along opposed side edge regions 30, 32. The liner sheet 14 is not secured to the backing sheet intermediate such joined regions so that it may be drawn upwardly from the backing sheet into contact with the wearer's body by operation of elastic members 44, 46. When this occurs a waste receiving pocket is produced within the garment to receive exudates from the wearer. Since separator sheet 18 is of a moisture pervious material, liquid may pass therethrough into and be received by absorbent pad 16.

Having illustrated and described the invention generally with respect to preferred embodiments, it should be apparent to those skilled in the art that modifications are possible without departing from the spirit of the invention.

What is claimed is:

1. An absorbent garment comprising:

a garment body having a longitudinal axis and a transverse axis and first and second waist edges at opposite sides of the transverse axis of the body and first and second side edges on opposite sides of the longitudinal axis of the body;

said body comprising a moisture impervious backing layer, a moisture pervious separator sheet, an absorbent core layer between said separator sheet and said backing layer, and a first inner layer;

said first inner layer is made from a single sheet having opposed faces and a waste receiving opening extending therethrough intermediate the first and second waist edges and the first and second side edges;

a first elongate elastic member is secured to one face of said first inner layer having a first end portion disposed between the first waist edge and the transverse axis and between the longitudinal axis and said first side edge, with remainder portions extending from said first end portion across the longitudinal axis between said first waist edge and said opening, along a side of said opening adjacent said second side edge, across the longitudinal axis between said opening and the second waist edge, and to a second end portion between the second waist edge and the transverse axis and between the longitudinal axis and said first side edge; and a second elongate elastic member secured to said one face of said sheet having a first end portion disposed between the first waist edge and the transverse axis and between the longitudinal axis and said second side edge, with remainder portions extending from said first end portion across the first elastic member between the first waist edge and said opening, along a side of said opening adjacent said first side edge, across the first elastic member between the opening and the second waist edge and to a second end portion between the second waist edge and the transverse axis and between the longitudinal axis and said second side edge;

said body further comprising a second inner layer secured to said one face of said first inner layer along the entire length of said first inner layer to enclose said elastic members therebetween;

wherein said first inner layer and said second inner layer are firmly secured to said separator sheet in a substantially leak-free manner.

2. The garment of claim 1, wherein said opening is elongate, having a long dimension and a relatively narrower dimension, and is disposed with its long dimension extending longitudinally of the garment.

3. The garment of claim 1, wherein said first inner layer and said second inner layer are formed from materials of differing hydrophobicity to thereby create a hydrophobic gradient between said first and second inner layers which enhances surface dryness.

4. The garment of claim 1, wherein said second inner layer has an opening defined therethrough which is substantially aligned with the opening in said first inner layer.

5. The garment of claim 1, wherein said first and second inner layers are moisture impervious.

6. The garment of claim 1, wherein the location at which said second elastic member crosses over the first elastic member is closer to the opening than to a waist edge of the garment.

7. The garment of claim 6, wherein said opening has an inner edge and said first and second elastic members in combination encircle said opening and are disposed a substantially constant selected distance from the inner edge of said opening.

8. The garment of claim 1, wherein said first and second elastic members are disposed in substantially mirror-image curvilinear paths.

9. An absorbent garment comprising:

a garment body having a longitudinal axis and a transverse axis and first and second waist edges at opposite sides of the transverse axis of the body and first and second side edges on opposite sides of the longitudinal axis of the body;

said body comprising a moisture impervious backing layer, a moisture pervious separator sheet, an absorbent core layer between said separator sheet and said backing layer and a first inner layer;

said first inner layer is made from a single sheet having opposed faces and a waste receiving opening extending therethrough intermediate the first and second waist edges and the first and second side edges;

a first elongate elastic member secured to one face of said sheet having a first end portion disposed between the first waist edge and the transverse axis and between the longitudinal axis and said first side edge, with remainder portions extending from said first end portion across the longitudinal axis between said first waist edge and said opening, along a side of said opening adjacent said second side edge, across the longitudinal axis between said opening and the second waist edge, and to a second end portion between the second waist edge and the transverse axis and between the longitudinal axis and said first side edge; and a second elongate elastic member secured to said one face of said sheet having a first end portion disposed between the first waist edge and the transverse axis and between the longitudinal axis and said second side edge, with remainder portions extending from said first end portion across the first elastic member between the first waist edge and said opening, along a side of said opening adjacent said first side edge, across the first elastic member between the opening and the second waist edge and to a second end portion between the second waist edge and the transverse axis and between the longitudinal axis and said second side edge;

wherein said first and second elastic members are disposed in substantially mirror-image curvilinear paths, and the curvilinear path for one of said elastic members resembles at least a portion of a substantially sine curve;

said body further comprising a second inner layer secured to said one face of said first inner layer along the entire length of said first inner layer to enclose said elastic members therebetween;

wherein said first inner layer and said second inner layer are firmly secured to said separator sheet in a substantially leak-free manner.

10. The garment of claim 9, wherein said one elastic member describes substantially a full phase of a sine curve between the first and second waist edges of the garment.

11. An absorbent garment comprising:

a garment body having a longitudinal axis and a transverse axis and first and second waist edges at opposite sides of the transverse axis of the garment and first and second side edges on opposite sides of a longitudinal axis of the body;

said body comprising a moisture impervious backing layer, a moisture pervious separator sheet, an absorbent core layer between said separator sheet and said backing layer, and a first inner layer;

said first inner layer is made from a single sheet having opposed faces and a waste receiving opening extending therethrough intermediate the first and second waist edges and the first and second side edges; and first and second elongate elastic members secured to one face of said sheet having laterally spaced first end portions disposed at opposite sides of the longitudinal axis of the garment and between the transverse axis and the first waist edge, and laterally spaced second end portions disposed at opposite sides of the longitudinal axis between the transverse axis and the second waist edge;

with the first and second ends of the first elastic member disposed on one side of the longitudinal axis and the first and second ends of the second elastic member on the opposite side of the longitudinal axis with remainder portions of said elastic members extending in substantially mirror-image curvilinear paths from said first end portions to said second end portions along opposite side margins of said opening;

where the mirror image paths of the first and second elastic members intersect one another;

said body further comprising a second inner layer secured to said one face of said first inner layer along the entire length of said first inner layer to enclose said elastic members therebetween;

wherein said first inner layer and said second inner layer are firmly secured to said separator sheet in a substantially leak-free manner.

12. The garment of claim 11, wherein the first end portion of said first elastic member is disposed between the first side edge and the longitudinal axis, and the first elastic member extends from said first end portion across the longitudinal axis between said first waist edge and said opening, along a side of said opening adjacent said second side edge, across the longitudinal axis between said opening and the second waist edge, and terminates at said second end portion between the longitudinal axis and said first side edge, and the first end portion of said second elongate elastic member is disposed between said longitudinal axis and said second side edge, and the second elastic member extends from said first end portion across the first elastic member between the first waste edge and said opening, along a side of said opening adjacent said first side edge, across the first elastic member between the opening and the second waist edge and terminates at said second end portion between said longitudinal axis and said second side edge.

13. The garment of claim 11, wherein said opening is elongate, having a long dimension and a relatively narrower dimension, and is disposed with its long dimension extending longitudinally of the garment.

14. The garment of claim 11, wherein said first inner layer and said second inner layer are formed from materials of differing hydrophobicity to thereby create a hydrophobic gradient between said first and second inner layers which enhances surface dryness.

15. The garment of claim 11, wherein said second inner sheet has an opening defined therethrough which is aligned with the opening in said first inner layer.

16. The garment of claim 11, wherein said first and second inner layers are moisture impervious.

17. The garment of claim 12, wherein the location at which said second elastic member crosses over said first elastic member is closer to the opening than to a waist edge of the garment.

18. The garment of claim 11, wherein said opening has an inner edge and said first and second elastic members in combination encircle said opening and are disposed a substantially constant selected distance from the inner edge of said opening.

19. An absorbent garment comprising:

a garment body having a longitudinal axis and a transverse axis and first and second waist edges at opposite sides of the transverse axis of the garment and first and second side edges on opposite sides of a longitudinal axis of the body;

said body comprising a moisture impervious backing layer, a moisture pervious separator sheet, an absorbent core layer between said separator sheet and said backing layer, and a first inner layer;

said first inner layer is made from a sheet having opposed faces and a waste receiving opening extending therethrough intermediate the first and second waist edges and the first and second side edges; and first and second elongate elastic members secured to one face of said sheet having laterally spaced first end portions disposed at opposite sides of the longitudinal axis of the garment and between the transverse axis and the first waist edge, and laterally spaced second end portions disposed at opposite sides of the longitudinal axis between the transverse axis and the second waist edge;

with the first and second ends of the first elastic member disposed on one side of the longitudinal axis and the first and second ends of the second elastic member on the opposite side of the longitudinal axis with remainder portions of said first and second elastic members extending in substantially mirror-image curvilinear paths from said first end portions to said second end portions along opposite side margins of said opening;

where the curvilinear paths of the first and second elastic members intersect each other, and the curvilinear path for one of said elastic members resembles at least a portion of a substantially sine curves;

said body further comprising a second inner layer secured to said one face of said first inner layer along the entire length of said first inner layer to enclose said elastic members therebetween;

wherein said first inner layer and said second inner layer are firmly secured to said separator sheet in a substantially leak-free manner.

20. The garment of claim 19, wherein said one elastic member describes substantially a full phase sine curve between said first and second waist edges of the garment.

* * * * *